United States Patent [19]

Dunlap

[11] Patent Number: 5,759,798
[45] Date of Patent: Jun. 2, 1998

[54] ASSAYS, TEST KITS AND BACTERIA FOR DETECTION OF AUTOINDUCERS

[75] Inventor: Paul Vernon Dunlap, Woods Hole, Mass.

[73] Assignee: Woods Hole Oceanographic Institution, Woods Hole, Mass.

[21] Appl. No.: 569,973

[22] Filed: Dec. 8, 1995

[51] Int. Cl.$^6$ .................................................. C12Q 1/02
[52] U.S. Cl. ........................................... 435/29; 435/6
[58] Field of Search .................................... 435/29, 6

[56] References Cited

U.S. PATENT DOCUMENTS

| | | | |
|---|---|---|---|
| 4,861,709 | 8/1989 | Ulitzur et al. | 435/6 |
| 5,082,785 | 1/1992 | Manning et al. | 435/252.32 |
| 5,196,318 | 3/1993 | Baldwin et al. | 435/69.1 |
| 5,221,623 | 6/1993 | Legocki et al. | 435/252.3 |
| 5,382,519 | 1/1995 | Dunlap et al. | 435/69.1 |
| 5,593,827 | 1/1997 | Bycroft et al. | 435/6 |

OTHER PUBLICATIONS

Dunlap, et al., *Journal of Bacteriology*, 1993, vol. 175, pp. 4615–4624.
Kuo et al., *Journal of Bacteriology*, 1994, vol. 176, pp. 7558–7565.
Gilson, et al., *Journal of Bacteriology*, 1995, vol. 177, pp. 6946–6951.
Kuo, et al., *Journal of Bacteriology*, 1996, vol. 178, pp. 971–976.
Young, et al., *Proc. Natl. Acad. Sci. USA*, 1983, vol. 80, pp. 1194–1198.
Lacombe, et al., *The Journal of Biological Chemistry*, 1986, vol. 261, pp. 16811–16817.
Callahan, et al., Abstract of the General Meeting of the American Society of Microbiology, p. 269.
Dunlap, et al., Abstract of the General Meeting of the American Society for Microbiology, p. 269.
Alper, et al., *Journal of Bacteriology*, 1975, vol. 122, pp. 1061–1090.
Ames, et al., *Journal of Bacteriology*, 1984, vol. 160, 1181–1183.
Barfield, et al., *Microbiol. Enzymes in Aquatic Environment*, Springer Berlay, 1991, pp. 239–248.
Beacham, et al., *Journal of General Microbiology*, 1980, vol. 119, pp. 31–34.
Botsford, *Microbiological Reviews*, 1981, vol. 45, pp. 620–642.
Botsford, *Journal of Bacteriology*, 1984, vol. 160, pp. 826–830.
Buettner, et al., *Journal of Bacteriology*, 1973, vol. 14, pp. 1068–1073.
Bullock, et al., *BioTechniques*, 1987, vol. 5, pp. 376–378.
Devreotes, *Science*, 1989, vol. 245, pp. 1054–1058.
Dunlap, et al., *Journal of General Microbiology*, 1992, vol. 138, pp. 115–123.
Francko, *Advances in Cyclic Nucleotides Research*, 1983, vol. 15, pp. 97–117.
Bengis–Garber, *Can. J. Microbiol.*, 1985, vol. 31, pp. 543–548.

(List continued on next page.)

*Primary Examiner*—James C. Housel
*Assistant Examiner*—Ginny Allen Portner
*Attorney, Agent, or Firm*—Linda M. Buckley; Peter F. Corless; Cara Z. Lowen

[57] ABSTRACT

The invention provides assays, kits and bacteria useful for detection of autoinducers. In a preferred aspect, the assay comprises 1) contacting a test sample suspected of containing an autoinducer with bacteria of the invention that are capable of producing an elevated amount of light in the presence of an exogenous autoinducer and that has at least two distinct genetic alterations that can each inhibit production of endogenous autoinducers; and 2) measuring the production of light. The sample will test positive for the presence of an autoinducer if a greater amount of light is produced relative to a control. The assays and kits have a variety of applications including use as an in vitro diagnostic for animal and plant disorders.

10 Claims, 1 Drawing Sheet

OTHER PUBLICATIONS

Monard, et al., *Biochemical and Biophysical Research Communications*, 1969, vol. 35, pp. 584–591.

RuBy et al., *Biol. Bull.*, 1976, vol. 151, pp. 574–586.

Saier, et al. *Journal of Biological Chemistry*, 1975, vol. 250, pp. 7593–7601.

Sanger, et al., *Proc. Natl. Acad. Sci.*, 1977, vol. 74, pp. 5463–5467.

Simon, et al., *Methods in Enzymology*, 1986, vol. 118, pp. 640–659.

Ullman, et al., *Advances in Cyclic Nucleotides Research*, 1983, vol. 15, pp. 1–53.

Dunlap, Abstract of the General Meeting of the 92nd American Society for Microbiology, p. 245.

Dunlap, Abstract of the 6th Int. Symp. on Microbial Ecology, SPAIN, 1992, p. 91.

Dunlap, et al., Abstract No. 179688 of the 93rd General Meeting, Atlanta, Ga., p. 5.

Callahan, et al., Abstract No. 115696 of the 93rd General Meeting, Atlanta, Ga., p. 5.

Williams, P. et al, FEMS Microbiol. Letts., vol. (100), pp. 161–168, 1992.

Swift, S. et al. Mol. Microbiol., vol. 10(3), pp. 511–520, 1993.

Eberhard, A et al, Arch. Microbiol., vol. 146 pp. 35–40, 1986.

Meigher, EA, Microbiol. Review, Mar., pp. 123–142 vol. 55(1), 1991.

Salmond, GPC et al, Mol. Microbiol, vol. 16(4) pp. 615–624, 1995.

Dunlap, PV et al, J. of Bacteriology, Apr., pp. 2440–2448, vol. 174(8), 1992.

Chhabra, SR et al, J of Antibiotics, Mar. vol. 46(3), pp. 441–454, 1993.

Jones, S et al, EMBO, vol. 12(6), pp. 2477–2482, 1993.

Pearson, J.P et al, Proc. Natl. Acad Sci. Jan., vol. 91, pp. 197–201, 1994.

Swift, S. et al, Trends in Microbiol, vol. 2(6) Jun., pp. 193–198, 1994.

Cui, Y et al, J. of Bacteriol, 3 Sep., pp. 5108–5115 vol. 177(7), 1995.

Fuqua, W.C et al, J. of Bacteriol., vol. 176(2), Jan. pp. 269–275, 1994.

Winsor, MK et al, Proc. Natl. Acad. Sci. Sep., vol. 92, pp. 9427–9431, 1995.

Kuo et al, J. of Bacteriology, Dec., vol. 176(24) pp. 7558–7565, 1994.

ASSAYS, TEST KITS AND BACTERIA FOR DETECTION OF AUTOINDUCERS

BACKGROUND OF THE INVENTION

Autoinducers (N-acyl-L-homoserine lactones, sometimes referred to herein as "AIs") are extracellular signal compounds used by a variety of bacteria to regulate cellular functions in response to high population density. For example, light production by the marine symbiotic bacterium *Vibrio fischeri* is controlled in a population density-responsive manner by the self-produced, membrane-permeable autoinducer, N-3-oxohexanoyl-L-homoserine lactone (N-3-oxohexanoyl-L-HSL; autoinducer-1; AI-1). AI-1 accumulates in a population density-dependent manner during bacterial growth. When it reaches a threshold concentration, AI-1, via the autoinducer receptor and transcriptional activator, LuxR, activates transcription of the lux operon, luxICDABEG, which encodes autoinducer synthase (luxI) and luminescence enzymes. (E. Eberhard et al., *Biochemistry*, 20:2444–2449 (1981); J. Engebrecht et al., *Cell*, 32:773–781 (1983); J. Engebrecht et al., *Proc. Natl. Acad. Sci. USA*, 81:4154–4158 (1984); B. Hanzelka et al., *J. Bacteriol.*, 177:815–817 (1995); G. Shadel et al., *J. Bacteriol.*, 172:3980–3987 (1990); J. Slock et al., *J. Bacteriol.*, 172:3974–3979 (1990); E. Swartzman et al., *J. Bacteriol.*, 172:6797–6802 (1990)). The autoinduction mechanism in *V.fischeri* also involves, among other regulatory aspects, an AI-1 mediated luxR negative autoregulation. (P. Dunlap et al., *J. Bacteriol.*, 170:4040–4046 (1988); P. Dunlap et al., *J. Bacteriol.*, 171:3546–3552 (1989); J. Engebrecht et al., *Genet. Eng.*, 8:31–44 (1986); G. Shadel et al., *J. Bacteriol.*, 173:568–574 (1991); G. Shadel et al., *J. Biol. Chem.*, 267:7690–7695 (1992)).

Long thought to be a regulatory mechanism unique to the luminescence system of *V.fischeri* and certain closely related marine luminous bacteria, autoinduction of gene expression recently has been identified in a wide variety of other bacteria (W. Fuqua et al., *J. Bacteriol.*, 176:269–275 (1994)). The diversity of species using autoinduction and the chemical and genetic similarities of their autoinduction systems indicate that autoinduction is an evolutionary conserved regulatory mechanism commonly used by bacteria to sense and respond to population density.

All bacteria presently known to utilize AIs associate with higher organisms, i.e., plants and animals, at some point during their lifecycles. For example, *Pseudomonas aeruginosa* is an opportunistic pathogen in humans with cystic fibrosis. *P.aeruginosa* regulates various virulence determinants with AI. Other examples of AI producing bacteria include *Erwinia carotovora*, *Pseudomonas aureofaciens*, *Yersinia enterocolitica*, *Vibrio harveyi*, and *Agrobacterium tumefaciens*. *E. carotovora* infects certain plants and creates enzymes that degrade the plant's cell walls, resulting in what is called "soft rot disease." *E. carotovora* produces the autoinducer N-3-oxohexanoyl-L-HSL. *Yersinia enterocolitica* is a bacterium which causes gastrointestinal disease in humans and has been reported to produce an autoinducer. *P.aureofaciens* associates with the roots of plants and produces antibiotics that block fungus growth in the roots. That antibiotic synthesis is under autoinducer control.

It thus would be desirable to have new methods for conveniently detecting autoinducers.

SUMMARY OF THE INVENTION

I have now discovered highly useful assays that can be employed to detect and analyze autoinducers and bacteria that produce same. The assays of the invention can be employed for a variety of applications including in vitro detection of animal and plant disorders.

More particularly, in one aspect, the invention provides a method of detecting autoinducer molecules in a test sample, the method comprising 1) contacting or admixing the test sample and bacteria of the invention (sometimes referred to herein as the "detection bacteria"), which bacteria are capable of producing an elevated amount of light in the presence of an exogenous autoinducer; and 2) measuring the production of light.

The detection bacteria preferably have at least two distinct genetic alterations, e.g. mutations, that each reduce production of endogenous autoinducers relative to an "unaltered" parent strain. Preferably, at least two distinct loci of the detection bacteria are altered so that production of endogenous autoinducer is reduced, e.g. as determined by assaying the detection bacteria for production of AI molecules relative to the AI molecules produced by an unaltered parent strain, or by other analysis. A detection strain of the invention with such multiple alterations can provide enhanced results in use in an assay or kit for the detection of exogenous autoinducers, specifically an enhanced response and sensitivity to the presence of exogenous autoinducers in a test sample relative to a strain without such multiple alterations.

A test sample will test positive for the presence of AIs if a greater amount of light is produced relative to a control (the control being the detection bacteria maintained under the same conditions but not contacted with the test sample).

The test sample suitably may be a biological fluid (e.g. human or other mammalian plasma sample), tissue homogenate, etc. The test sample also may comprise a medium conditioned by the growth of bacteria suspected of autoinducer production.

The detection bacteria can be naturally occurring or mutant bacteria which are capable of producing a detectable amount of light in the presence of exogenous autoinducers. Preferably the detection bacteria produce less light in the absence of exogenous autoinducers relative to light produced by the strain in the presence of such autoinducers, and more preferably the bacteria produce no or essentially no detectable light in the absence of exogenous autoinducers.

Mutated detection bacteria are generally preferred. Particularly preferred are mutant bacteria obtained from a parent strain that is capable of luminescence and production of an endogenous autoinducer. Preferred mutants include those that lack more than one functional autoinducer synthase locus of a parent strain, thereby further minimizing or even eliminating production of endogenous luminescence autoinducers (i.e. such autoinducers that can invoke light production) by the mutant.

The invention also includes detection bacteria strains and methods for obtaining such strains.

In one aspect, the methods include selection of naturally occurring bacteria to identify isolated strains that produce low levels of light in the absence of exogenous autoinducers, and more preferably no or essentially no detectable (naked eye examination) light, but that produce a detectable amount of light in response to an exogenous autoinducer.

In other aspects, mutant bacteria are produced through mutating at least one, and preferably at least two, genes that participate in a parent strain's autoinducer synthetic pathway. Preferably, the mutated gene is an autoinducer synthase locus, the mutation of which prevents or inhibits accumulation of endogenous autoinducers. Mutants of *Vibrio fis-*

*cheri* are specifically preferred, including those lacking functional luxI (the AI-1 synthase locus) genes. More preferred are *V.fischeri* mutants that lack functional luxI and ainS (the AI-2 synthase locus) genes, i.e. the production by the mutant of endogenous N-3-oxohexanoyl-L-homoserine (AI-1) and N-octanoyl-L-homoserine is at least inhibited relative to a strain having functional ainS and luxI sites. (See L. Gilson et al., *J. Bacteriol.*, 177(23):6946–6951 (1995); and A. Kuo et al., *J. Bacteriol.*, 176(24):7558–7565 (1994) regarding the luxI and ainS sites).

MJ-215 Accession No. 55731 is a particularly preferred mutant of the invention, lacks functional ainS and luxI components, produces no or essentially no visible light (naked eye examination; darkened room) in the absence of exogenous AIs, and produces light upon exposure to exogenous AIs. *V.fischeri* MJ-211 is also a preferred mutant of the invention and lacks a functional luxI gene, i.e. the mutant does not accumulate AI-1.

The present invention further provides in vitro kits for detecting autoinducers in test samples. Other aspects of the invention are disclosed infra.

DETAILED DESCRIPTION OF THE INVENTION

Figure 1:
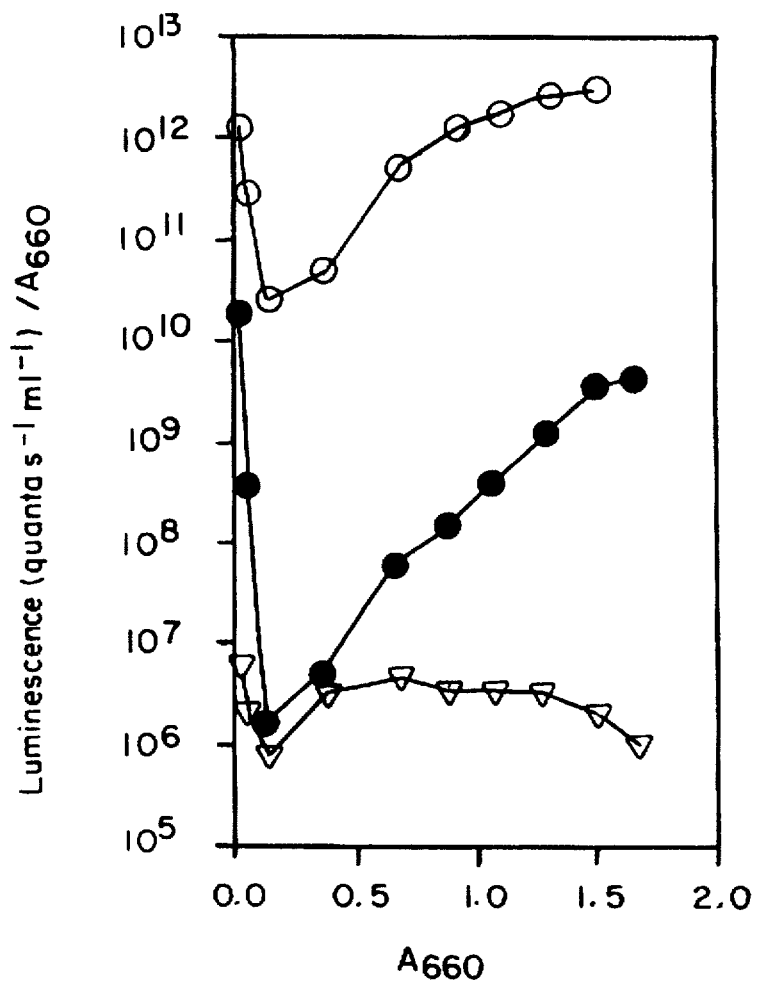
FIG. 1 shows luminescence induction behavior of luxI and luxI ainS mutants of *V.fischeri*. Luminescence (quanta $s^{-1}$ $ml^{-1}/A_{660}$) during growth ($A_{660}$) of MJ-100 (luxI$^+$an$^+$) (O), MJ-211 (ΔluxI) (●), and MJ-215 (ΔluxI ainS) (∇).

The present invention provides highly useful and convenient methods of detecting autoinducer molecules. Moreover, by detection of an AI marker, the assays of the invention can detect the corresponding bacteria as well as disorders mediated by or otherwise relating to such bacteria.

The assay of the invention can be useful in detecting autoinducers in a wide variety of sample types such as e.g. human or other mammalian biological fluids or tissue homogenates, or a medium conditioned by the growth of bacteria suspected of producing AIs (sometimes referred to herein as the "test bacteria"). Such samples can be prepared by methods generally known in the art. Preferably in preparing samples of biological fluids, the cells are removed by methods known in the art, such as centrifugation or filtration. Samples of tissue, e.g. mammalian or other animal or plant tissue, are preferably homogenized in a suitable solution, e.g. sodium chloride, and the debris (e.g., cells, bacteria, cell debris) removed, for example by subjecting the homogenate to a slow spin in a centrifuge.

When the sample comprises a medium conditioned by the growth of bacteria ("test bacteria") suspected of autoinducer production, conditioning can be carried out by growing the bacteria to be tested for autoinducer production in a suitable complete liquid medium. The test bacteria are preferably grown to a high cell density. For example, the test bacteria are grown to a cell density which has a detectable absorbance or a cell density greater than about $10^8$ cells m$l^{-1}$. The test bacterial cells then may be removed from the medium by methods known in the art, such as by centrifugation and filtration. The autoinducers, if produced by the bacteria, are present in the conditioned medium. The resulting conditioned medium can be used in an assay immediately, or stored frozen (e.g., at −20° C.) until assayed.

The detection bacteria of the invention are contacted with the test sample suspected of containing an autoinducer (such as those samples described above), typically in a solution that will not deleteriously affect the bacteria. For example, the test sample and the detection bacteria can be admixed in a standard buffer solution. The test sample and detection bacteria also may be admixed in a growth medium for the detection bacteria, but use of such medium is not required. It is preferred that a control assay lacking the test sample is also prepared and maintained under identical or essentially identical conditions as the admixture of the test sample and detection bacteria. The production of light in an amount greater than that produced by a control sample indicates the presence of autoinducer in the test sample. A 10-times or greater difference in light production (e.g. as measured by a standard photometer) between test and control assays is clearly indicative of the presence of autoinducers in the test sample.

The detection bacteria may be selected naturally occurring bacteria or mutant bacteria that produce a detectable amount of light in the presence of exogenous autoinducers. That is, the detection bacteria produce a measurable light differential in the presence of an exogenous autoinducer in comparison to an absence of exogenous autoinducer, especially an elevated amount of light in the presence of an exogenous autoinducer.

Such light production differentials may be conveniently detected by simple naked eye inspection and/or by analytical tools such as a standard photometer-photomultiplier, x-ray or photographic film, and the like. Analysis of light production will be facilitated (and may be generally necessary in many cases) by inspecting for light production under darkened conditions, e.g. a darkened room or viewing chamber.

The mutant detection bacteria are preferably prepared from a parent strain capable of bioluminescence, i.e. the bacteria are capable of producing light that may be detected by the naked eye or other appropriate detection device such as a photometer, film, etc. Mutation may be carried out by a variety of techniques, e.g. exposure to ultraviolet light or other radiation, treatment with a mutagen such as nitrosoguanidine and the like, and/or direct genetic deletion or other manipulation. The mutagenesis treatment desirably decreases or inhibits normal luminescence of the strain, particularly as may be induced by an endogenous autoinducer, while capability for bioluminescence in response to exogenous autoinducers is maintained. Thus, the mutation preferably alters one or more reading frames that code for endogenous autoinducers, particularly endogenous luminescence autoinducers, to prevent accumulation of such autoinducers.

Following the mutagenesis step, an appropriate selection protocol is conducted such as culturing the mutated strains in a growth medium and selecting mutants that exhibit a decreased level of endogenous induction of luminescence and can provide a detectable amount of luminescence in the presence of an exogenous autoinducer.

Genetic deletion/replacement, or other manipulation is a preferred form of mutagenesis. As mentioned above, preferred parent strains are capable of bioluminescence and producing autoinducers themselves, and the genetic manipulation alters at least one genetic component in the autoinducer synthetic pathway of the strain so that endogenous autoinducer production is at least inhibited, while capability for bioluminescence in response to exogenous autoinducers is maintained. While genetic deletion is a preferred mutagenesis technique, other manipulations that alter reading frame(s) that code for endogenous autoinducers also can be employed. For example, a transposon can be inserted into a sequence coding for an autoinducer, or a simple point mutation can be made in such sequence. Such genetic deletion and other mutation procedures are generally known in the art and described e.g. in Sambrook, et al., *Molecular Cloning* (2d ed. 1989); and F. Ausubel et al., *Current Protocols in Molecular Biology*, John Wiley, New York (1987).

Preferred mutants may then be selected by screening for those mutants that produce a measurable greater amount of light in the presence of exogenous autoinducer and the production of relatively less light in the absence of such autoinducer. See, for instance, the Scheme and Example 1(C) which follows.

Preferably, the mutated component of the detection bacteria is an autoinducer synthase locus, and the mutation prevents or at least inhibits the accumulation of the endogenous autoinducer as discussed above. Such mutation can be verified by assaying the mutant for production of AI molecules. See, for instance, the Scheme below and Example 1 which follows.

Also, as discussed above, preferably, more than one genetic component may be mutated, e.g. more than one autoinducer synthase locus can be mutated. Such additional genetic manipulation will be particularly appropriate for parent strains that produce multiple types of autoinducers and should further decrease the production of endogenous autoinducers so that the resultant mutant will produce a detectably lower amount of light in the absence of exogenous autoinducers.

Particularly preferred detection bacteria are mutated *Vibrio fischeri* strains, especially strains that have mutated (e.g. deleted) luxI and/or ainS sites, which can be conveniently produced through genetic engineering techniques. See, for instance, the examples which follow. Such mutations can prevent the endogenous production of autoinducers whose synthesis is directed by the luxI and ainS genes. Other preferred detection bacteria will be selected naturally occurring or mutated proteobacteria that are symbionts or pathogens of higher organisms and that produce one or more AIs.

More specifically, one preferred mutation protocol involves inactivating the luxI and preferably also the ainS genes of *V.fischeri*, by deletion of cloned genes in vitro, followed by recombinational replacement of the wild-type genes in *V.fischeri* with the mutated forms whereby the resulting mutant does not produce the corresponding autoinducers. In *V.fischeri*, disabling the two genes (i.e. both luxI and ainS) eliminates the ability of the bacterium to produce the luxI-dependent luminescence autoinducers, AI-1 and AI-3, and the ainS-dependent luminescence autoinducer, AI-2. Such a protocol is detailed in the below Scheme as well as in the examples which follow, which disclose the preparation of the detection bacteria *V.fischeri* MJ-211 and *V.fischeri* MJ-215. See also A. Kuo et al., *J. Bacteriol.*, 176(24):7558–7565 (1994) for MJ-211.

SCHEME

1. Construction of a mutation in the cloned luxI gene
pNL121 (pSUP102 + 9 kb lusR luxICDABEG)

| partial digest with SfcI
| briefly digest with exonuclease III
| blunt-end with Klenow
| ligate
↓

-continued
SCHEME

Vector with putative deletion in luxI

| confirm that *E.coli* transformed with vector produces a high level
| of light only in response to exogenously added autoinducer
| (non-polar mutation) determine size of deletion in luxI by gel
| electrophoric analysis of vector
↓ pAK211 (pNL121 with 250-bp non-polar deletion in luxI)

2. Construction of the luxI deletion mutant *V. fischeri* MJ-211
pAK211

| conjunctively transfer vector from *E.coli* S17-1 to MJ-100
| (spontaneous Nx$^r$ derivative of wild-type *V.fischeri* MJ-1)
| screen transconjugant *V. fischeri* for Nx$^r$Cm$^s$ (loss of vector)
| and for lack of high level of light (mutation in luxI replaces
| wild-type luxI)
↓

Putative luxI deletion mutant

| confirm deletion with Southern hybridization analysis
| confirm inability to produce AI-1
| confirm ability to respond to AI-1 with high level of light
↓

MJ-211

3. Construction of a mutation in the cloned ainS gene
pAI009 (pSUP102 + 2.7-kb ainS fragment)

| partial digest with ClaI
| blunt-end 2-bp overhang with Klenow
| ligate
↓

Vector with putative ainS mutation

| confirm that *E.coli* transformed with vector makes no AI-2
↓ pAI015 (pAI009 with 2-bp deletion in ainS)

4. Construction of the double luxI ainS mutant *V.fischeri* MJ-215
pAI015

| conjugatively transfer vector from *E.coli* S17-1 to MJ-211
| screen transconjugant *V.fischeri* for Nx$^r$Cm$^S$ (loss of vector)
| and for lack of light detectable by eye (mutation on ainS
| replaces wild-type ainS)
↓

Putative luxI ainS double mutant

| confirm loss of ClaI site with Southern hybridization analysis
| confirm lack of autoinducer synthesis
| confirm introduction of pAI009, but not pSUP102 or pAI015,
| restores luminescence
↓

MJ-215

That gene replacement strategy described in the above Scheme also can be employed to prepare other mutant detection bacteria of the invention, i.e. by use of restriction enzymes to delete gene(s) that code for endogenous autoinducers, cloning the digested DNA into a suitable vector and then transform a suitable host cell such as *E.coli* with such vector and then transfer that vector back to a parent strain and screen for the desired mutants, e.g., the transconjugant with decreased bioluminescence in the absence of exogenous autoinducers. The successful deletion can be confirmed a number of methods, e.g. Southern hybridization analysis, the lack of production of one or more endogenous autoinducers and/or the ability of the mutant to produce a detectable amount of light in response to exogenous autoinducers.

Multiple distinct genetic alterations can be made by repeating the above, but deleting another gene, i.e. delete gene(s) that code for other endogenous autoinducers, clone the digested DNA into a suitable vector and then transform a suitable host cell such as *E.coli* with such vector. That vector then can be transferred back to the previously prepared mutant that contains the distinct genetic alteration and the transconjugant screened for the desired "multiple" or "double" mutant and screen for the desired mutants. For example, the transconjugants can be screened for a decreased amount of light produced relative to the progenitor single mutation strain. Again, that a desired mutant having multiple genetic alterations is in hand can be confirmed such as by Southern hybridization analysis, the lack of production of one or more endogenous autoinducers and/or the ability of the mutant to produce a detectable amount of light in response to exogenous autoinducers.

Still further genetic alterations can be made in the same manner where a vector containing the further mutation is transferred into the "double" mutant.

Preferably the mutations do not substantially interfere with the luminescence system of the bacterium so that the mutated bacterium can produce light in response to exogenous autoinducers. Thus, for example, with regards to mutation of the luxI gene of *V.fischeri* as discussed above, preferably the mutation permits expression from the luxI promoter to continue through the contiguous luxCDABEG genes, i.e. the mutation is non-polar. Such a non-polar mutation, while disabling the bacterium's ability to produce AI-1 and AI-3, permits the luminescence system to operate to produce light in response to exogenous autoinducers that activate lux operon transcription via LuxR protein. The preferred mutational inactivation of ainS in addition to luxI further reduces to background the level of luminescence produced by *V.fischeri* containing an otherwise intact luminescence system, thereby strongly enhancing the sensitivity and range of response of the detection bacteria to exogenous autoinducers.

In a particularly preferred assay of the invention a *V.fischeri* mutant is the detection bacterium and is contacted with a test sample. That mixture is admixed with with a buffer such as artificial seawater hepes containing 10 mM Tris (pH 7.0) or a suitable growth medium such as artificial seawater hepes (ASH) broth. The test mixture should be mixed with the buffer or growth medium in a ratio to sufficient to sustain the detection bacteria, e.g. a ratio of test mixture:buffer/growth medium of about 1:1 or higher. The mixture is then maintained under conditions sufficient to sustain the detection bacteria and light production periodically monitored. See the examples which follow for exemplary conditions.

As discussed above, useful detection bacteria also can be obtained by screening naturally occurring bacteria to select for bacteria capable of producing light in the presence of exogenous autoinducers and production of comparatively lower levels of light in the absence of exogenous autoinducers, and more preferably the production of essentially no detectable light in the absence of such autoinducers. Again, the selected detection bacteria should have at least one genetic alteration, and preferably at least two distinct genetic alterations, from a normal strain that each reduce production of endogenous autoinducers. Preferably, at least two loci of the detection bacteria are altered so that production of endogenous luminescence autoinducer is reduced, more preferably substantially or completely eliminated (e.g. reduction of at least about 90%, 95% or 98% relative to the parent strain).

The autoinducer molecules that can be identified by the assays of the invention can be a wide variety of N-acyl-homoserine lactones including, e.g., N-octanoyl-L-homoserine lactone, N-3-oxohexanoyl-L-homoserine lactone, N-hexanoyl-L-homoserine lactone and the like.

The test bacteria may vary widely among bacteria that produce an autoinducer and include e.g. *Pseudomonas aeruginosa*, *Vibrio fischeri*, *Erwinia carotovora*, *Yersinia enterocolitica* and the like. Other bacteria that produce autoinducers are known and can be detected by assays of the invention. For example, *Agrobacterium tumefaciens* and *Pseudomonas aureofaciens* may produce autoinducers that will be detected by at least some detection bacteria of the invention.

Light produced by detection bacteria in response to the presence of autoinducers will be within the blue/green visible range and can be detected by methods known in the art. For example, in addition to naked eye inspections, a variety of detection devices can be employed such as standard laboratory photometers with a photomultiplier. See also P. Dunlap et al., *J. Bacteriol.*, 171:3549-3552 (1992), for exemplary equipment and methods to measure light of bioluminescent bacteria. Other detection methods and materials include spotting or placing the resulting assay mixture onto or near x-ray or photographic film. An image that develops on the film with more intensity relative to a control provides a positive reading for the presence of an autoinducer in the test sample.

Measurements for light production by the detection bacteria in the assay mixture are suitably taken over a period of time, preferably at regular intervals. For example, in one preferred protocol, measurements are taken at 30 minute intervals, or more frequently, for 3 to 5 hours after commencing culturing of the detection bacteria and test sample.

Light production in the assay cultures that contain test sample is compared with the levels of light produced by control cultures, i.e. essentially identical cultures that contain the detection bacteria but not the test sample. The production of light of an intensity by the assay culture above the basal level of the control indicates the presence of an autoinducer in the test sample. For example, as mentioned above, the production of 10 or more times more light in the assay sample as compared with the control is indicative of the presence of autoinducer in the test sample.

The invention also includes diagnostic kit formulations. Kits of the invention preferably include detection bacteria for use in the assay in an immediately usable or readily reconstituted form and preferably any other reagents necessary to ensure the activity and/or growth of the bacteria. Optionally, the kit includes a detection device to facilitate determination of whether the test sample contains an autoinducer.

More particularly, in certain preferred kits of the invention, the kit includes a vial or vessel containing freeze-dried bacteria and an ampule or vial containing growth medium to revive and sustain the bacteria. Such a kit may also include photographic or x-ray film or other detection device. In use, the detection bacteria are mixed with the growth medium and the test sample of interest added. After a predetermined period of time, an aliquot of the assay mixture is spotted on or placed near the film, and the film is developed. A spot on the film indicates the presence of autoinducer in the sample. Preferably a control, containing the detection bacteria and growth medium, but not the test sample, is run simultaneously. A detectable spot on the film for the mixture containing the test sample, and the absence of or less prominent spot for the control, is indicative of the presence of an autoinducer in the test sample.

Kits of the invention also may include an absorbent material such as filter paper, or other appropriate material, to which the detection bacteria and test sample may be applied and analyzed. In use, the test sample is added to the filter paper or other material (e.g. spotted) where the detection bacteria have been previously or will be applied (the filter paper is kept moist to ensure survival of the detection bacteria). The test sample and the detection bacteria are also preferably each applied to separate areas of the filter paper to provide controls.

As discussed above, the assays, kits and bacterial strains of the invention may be employed as a diagnostic tool for medical disorders such as e.g. cystic fibrosis, gastrointestinal disease mediated by or otherwise involving Yersinia enterocolitica or other bacteria that produces an autoinducer as well as for detection of agricultural infections such as soft rot disease or the presence of P.aureofaciens with selected vegetation. For example, a plasma sample can be obtained from a mammal such as a human, or alternatively a human or other mammalian tissue sample or a plant sample may be obtained, and used as a test sample in the assay of the invention, i.e. contacted with detection bacteria and the mixture incubated under growth conditions. Light production above the level of a control will indicate the presence of an autoinducer in the plasma test sample and thus that the patient is infected with corresponding bacteria.

Detection bacteria also may be used in the assays and kits of the invention that are more responsive to a particular autoinducer, such as the autoinducer that is a marker for cystic fibrosis, so that the assay or kit will provide more exacting diagnostic information. Such specific detection bacteria can be readily identified by testing various strains against a known autoinducer. Also, such detection bacteria may be obtained by mutation of a bacterial strain that produces an autoinducer that is to be assayed.

All documents mentioned herein are incorporated herein by reference in their entirety.

The following non-limiting examples are illustrative of the invention.

EXAMPLE 1

Preparation of Detection Bacteria (A) Bacterial strains and plasmids.

Derivatives of *E.coli* K-12 and *V.fischeri* MJ-1 were employed for preparation of mutants by genetic deletion. *E.coli* JM83 (C. Yanisch-Perron et al., *Gene*, 33:103–119 (1985)) was used for most cloning manipulations, which followed standard procedures (F. Ausubel et al., *Current Protocols in Molecular Biology*, John Wiley, New York, 1987)). *E.coli* S17-1 is a strain capable of conjugatively transferring the mobilizable chloramphenicol-resistance (Cm$^r$) plasmid pSUP102 to a wide range of recipients (R. Simon et al., *Methods Enzymol.*, 118:640–659 (1986)), including *V.fischeri* (P. Dunlap et al., *J. Bacteriol.*, 174:3549–3552 (1992); A. Kuo et al., *J. Bacteriol.*, 176:7558–7565 (1994)). *V.fischeri* MJ-100 is a spontaneously nalidixic acid resistant (Nx$^r$) derivative of the wild-type *V.fischeri* strain MJ-1 (P. Dunlap et al., *J. Bacteriol.*, 174:3549–3552 (1992); E. Ruby et al., *Biol. Bull. Woods Hole*, 141:574–586 (1976)).

pAK411 contains the *V.fischeri* MJ-1 lux genes (J. Engebrecht et al., *Cell*, 32:773–781 (1983)) cloned into pBR322, with a nonpolar deletion in luxI (A. Kuo et al., *J. Bacteriol.*, 176:7558–7565 (1994)). JM83 containing pAK411 produces visible luminescence, but only in the presence of a source of exogenous autoinducer. pAK011 is an 11.8 kb BglII fragment from pJR551, which contains the lux genes with a lacZ fusion in the luxR and a point in luxI (P. Dunlap et al., *J. Bacteriol.*, 171:3549–3552 (1989)), cloned into the BamHI site of pSUP102. pAI009, which directs the synthesis of AI-2 in JM83, is pSUP102 containing the 2.7 kb HindIII ainS fragment from MJ-1 (Gilson et al., *J. Bacteriol.*, 177(3):6946–6951 (1995)). Other plasmids were constructed using standard procedures as indicated below.

(B) Culture conditions and physiological assays.

*E.coli* strains were maintained on LB medium (F. Ausubel et al., Current Protocols in Molecular Biology, John Wiley, New York, (1987)) with appropriate antibiotics to assure plasmid maintenance. *V.fischeri* strains were maintained on solid LBS medium (P. Dunlap et al., *J. Bacteriol.*, 171:3549–3552 (1992)), with nalidixic acid for MJ-100 and its derivatives. *E.coli* liquid cultures were grown in LB with 50 mM Tris (pH 7.5) and an appropriate antibiotic, whereas liquid cultures of *V.fischeri* were grown in artificial seawater hepes (ASH) medium (P. Dunlap et al., *J. Bacteriol.*, 171:3549–3552 (1992)) without antibiotics except as indicated. Antibiotics were used at the following concentrations: Nx, 20 mg l$^{-1}$; Ap, 150 mg l$^{-1}$; Cm, 34 mg l$^{-1}$; Km, 20 mg l$^{-1}$; and Nm, 200 mg l$^{-1}$, except as indicated otherwise. Growth conditions and measurement (absorbance at 660 nm; $A_{660}$), luminescence assays, and the light-measuring equipment and standard were as previously described in P. Dunlap et al., *J. Bacteriol.*, 171:3549–3552 (1992).

Autoinducer activity in media conditioned by the growth of bacteria was assayed by measuring the luminescence response of *E.coli* PD100 (pJR551, pPD749), as described previously, (P. Dunlap et al., *J. Bacteriol.*, 171:3549–3552 (1989); A. Kuo et al., *J. Bacteriol.*, 176:7558–7565 (1994)). Where distinction between the different *V.fischeri* autoinducers was required, samples were fractionated by reversed phase high-pressure liquid chromatography (RP HPLC) and the fractions were assayed for autoinducer activity (A. Kuo et al., *J. Bacteriol.*, 176:7558–7565 (1994)). Synthetic autoinducers were added to culture tubes as solutions in chloroform, and the solvent was removed by drying with a stream of air before the culture medium and bacteria were added.

(C) Construction of *V.fischeri* ainS mutants.

The ainS plasmid pAI015 was constructed by digesting pAI009 (see Gilson et al. supra), with ClaI (one site in ainS, one site vector), blunt-ending, gel-purifying singly-cut plasmid, and ligating. The resulting plasmid theoretically has a frameshifting 2-bp insertion in ainS that eliminates the ClaI site. JM83 (pAI015) was Cm$^r$ and did not produce AI-2. The *V.fischeri* ΔluxI ainS double mutant MJ-215 was constructed by conjugatively transferring pAI015 from *E.coli* S17-1 to MJ-211 and screening the transconjugant *V.fischeri* for Nx$^r$ Cm$^s$ recombinants that emitted no light detectable by eye. Southern analysis confirmed that MJ-215 lacked the ClaI site in ainS. MJ-215 synthesized no autoinducer activity detectable by the PD100 (pJR551, pPD749) assay (see Dunlap et al., *J. Bacteriol.*, 170:4040–4046 (1988); and Dunlap et al., *J. Bacteriol.*, 171:3549–3552 (1989)), but it responded to the addition of synthetic autoinducers by emitting light. Introduction of pAI009, but not of pSUP102 or pAI015, restored luminescence in MJ-215. Samples of *Vibrio fischeri*, strain MJ-215 have been deposited with the American Type Culture Collection (ATCC), 12301 Parklawn Drive, Rockville, Md. 20852 on Dec. 8, 1995 and given Accession No. 55731. MJ-215 does not produce the three luminscent autoinducers—AI-1, AI-2 and AI-3—produced by normal V.fischeri cells (see Kuo, J. Bacteriol., 176: 7558 (1994); and Gilson et al., J. Bacteriol., 177(3):6946–6951 (1995)). MJ-215 grew at a rate essentially identical to that of the parent strain, MJ-100, and to that of its direct progenitor strain, MJ-211 (ΔluxI asnS⁺). However, in contrast to MJ-100 and MJ-211 (see Dunlap et al., J. Bacteriol., 174:2440–2448 (1992) and Kuo et al., J. Bacteriol., 176:7558–7565 (1994)), MJ-215 did not induce luminescence. See FIG. 1 of the drawings.

EXAMPLE 2

Consistent with the lack of induction, culture medium conditioned by the growth of MJ-215 contained no autoinducer activity detectable with a sensitive assay for N-acyl-L-HSLs that activate lux operon transcription via LuxR. The addition of AI-1 or AI-2 nonetheless strongly stimulates luminescence in MJ-215, indicating the mutant responds to exogenous autoinducers. For example, MJ-215 at an $A_{660}$ of 0.5 produced approximately $8 \times 10^8$ quanta $s^{-1}$ $ml^{-1}$ in the presence of 750 nM AI-2, compared to approximately $2 \times 10^6$ quanta $s^{-1}$ $ml^{-1}$ with no addition. Furthermore, the production of light by the mutant in the presence of exogenous AI-2 demonstrates that this compound, in the absence of AI-1, activates lux operon transcription in V.fischeri (A. Kuo et al., J. Bacteriol., 176:7558–7565 (1994)). Results are further disclosed in Tables 1 and 2 below.

TABLE 1

Luminescence of E. coli PD100 (pJR551, pPD749) and V. fischeri MJ-215 (pAK011)

| Strain | Addition | Luminescence[a] |
|---|---|---|
| PD100 (pJR551, pPD749) | None | $2.2 \times 10^8$ |
|  | AI-1 (160 nM) | $8.1 \times 10^{11}$ |
|  | AI-2 (7.1 μM) | $7.4 \times 10^{11}$ |
| MJ-215 (pAK011)[b] | None | $2.3 \times 10^7$ |
|  | AI-1 (300 nM) | $7.8 \times 10^{10}$ |
|  | AI-2 (7.5 μM) | $2.0 \times 10^{10}$ |

[a]Quanta $s^{-1}$ $ml^{-1}$ at $A_{660}$ of 1.0 E. coli and 1.1 for V. fischeri.
[b]Grown in the presence of 17 mg $l^{-1}$ chloramphenicol to assure plasmid maintenance.

TABLE 2

Luminescence of E. coli JM83 (pAK011, pAK411)

| Addition(s) | Luminescence[a] |
|---|---|
| None | $8.0 \times 10^6$ |
| AI-1 (50 nM) | $4.3 \times 10^8$ |
| AI-2 (1.5 μM) | $1.0 \times 10^7$ |
| AI-1 and AI-2 | $5.4 \times 10^7$ |

[a]Quanta $s^{-1}$ $ml^{-1}$ at $A_{660}$ of 0.27.

EXAMPLE 3

Assay for exogenous AI in test sample

Bacteria to be tested for autoinducer production are grown in a suitable complete liquid medium, under conditions appropriate for that species, to a high cell density (e.g., above an absorbance at 660 nm ($A_{660}$) or $>10^8$ cells $ml^{-1}$). The bacterial cells are then removed by centrifugation and filtration. The resulting "conditioned medium" is stored frozen at −20° C. until assayed.

Cells of a suitable detection bacterial strain such as MJ-215 are grown overnight in artificial seawater hepes (ASH) broth at 28° C. with moderate aeration, as generally described for normal V.fischeri in Dunlap and Kuo, 1992, J. Bacteriol., 174:2440–2448.

Conditioned medium is then mixed one-to-one with ASH broth (3 ml total volume in 13 mm diameter tubes), or in higher ratios, and detection bacteria such as MJ-215 are inoculated into the medium at an $A_{660}$ of approximately 0.10 and incubated with aeration as described above for the growth of V.fischeri. Unconditioned medium mixed with ASH medium in the same ratio, as a control, is also inoculated and incubated. Alternatively, the conditioned medium or other test sample can be mixed with the detection bacteria in a suitable buffer such as artificial seawater hepes containing 10 mM Tris (pH 7.0) rather than a growth medium.

Light production of the test sample/detection bacteria mixture is monitored at 30 minute intervals, or more frequently, for 3 to 5 hours using any standard laboratory photometer-photomultiplier.

Light production in the test sample/detection bacteria mixture substantially above the low basal level in the control (e.g. about $10^1$ to $10^6$ or more-fold more light) indicates the presence of an autoinducer in the test sample.

The present invention has been described in detail, including the preferred embodiments thereof. However, it will be appreciated that those skilled in the art, upon consideration of the present disclosure, may make modifications and/or improvements of this invention and still be within the scope and spirit of this invention as set forth in the following claims.

What is claimed is:

1. An assay for detecting an autoinducer molecule in a test sample comprising:
   contacting the test sample with bacteria comprising Vibrio fischeri which have autoinducer synthetic pathways which will produce, a detectable amount of light in response to an exogenous autoinducer, the bacteria having at least two distinct alterations in the geneloci that participate in the autoinducer pathways that each inhibit production of endogenous autoinducers; and
   measuring light produced by the bacteria.

2. The assay of claim 1 wherein light measured in an amount greater than that produced by the bacteria in the absence of the test sample indicates the presence of autoinducer in the test sample.

3. The assay of claim 1 wherein the sample is selected from a biological fluid, tissue homogenate or medium conditioned by the growth of a test bacteria suspected of autoinducer production.

4. The assay of claim 1 wherein the test sample is obtained from a mammal or plant.

5. The assay of claim 1 wherein the autoinducer is produced by a bacteria selected from the group consisting of Vibrio fischeri, Erwinia carotovora and Yersinia enterocolitica.

6. The assay of claim 1 wherein the bacteria are a mutated strain.

7. The assay of claim 6 wherein the mutation inhibits production of endogenous autoinducer.

8. The assay of claim 1 wherein the bacteria are mutants of a parent strain that is bioluminescent and capable of producing an autoinducer.

9. The assay of claim 1 wherein the alterations comprise mutations in luxI and ainS sites.

10. The assay of claim 1 wherein the bacteria comprises MJ-215 (ATCC Accession No. 55731).

* * * * *